(12) United States Patent
Zhao

(10) Patent No.: US 9,333,365 B2
(45) Date of Patent: *May 10, 2016

(54) ANTENNA FOR AN IMPLANTABLE MEDICAL DEVICE

(75) Inventor: Yanzhu Zhao, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 491 days.

This patent is subject to a terminal disclaimer.

(21) Appl. No.: 12/847,043

(22) Filed: Jul. 30, 2010

(65) Prior Publication Data

US 2012/0029598 A1   Feb. 2, 2012

(51) Int. Cl.
| A61N 1/08 | (2006.01) |
| A61N 1/372 | (2006.01) |
| A61B 5/00 | (2006.01) |
| A61B 5/0215 | (2006.01) |
| A61B 5/11 | (2006.01) |

(52) U.S. Cl.
CPC .......... *A61N 1/37211* (2013.01); *A61B 5/0031* (2013.01); *A61B 5/0215* (2013.01); *A61B 5/6876* (2013.01); *A61B 5/6882* (2013.01); *A61B 5/1122* (2013.01); *A61B 2562/0219* (2013.01)

(58) Field of Classification Search
USPC ...................................... 623/1.15; 607/32, 60
See application file for complete search history.

(56) References Cited

U.S. PATENT DOCUMENTS

| 2,324,462 A | 7/1943 | Leeds et al. |
| 4,542,532 A | 9/1985 | McQuilkin |
| 5,058,581 A * | 10/1991 | Silvian ............................ 607/32 |
| 5,285,210 A | 2/1994 | Sato et al. |
| 5,438,699 A | 8/1995 | Coveley |
| 5,562,713 A | 10/1996 | Silvian |
| 6,057,803 A | 5/2000 | Kane et al. |
| 6,221,024 B1 | 4/2001 | Miesel |
| 6,295,473 B1 | 9/2001 | Rosar |
| 6,298,271 B1 | 10/2001 | Weijand |
| 6,418,004 B1 | 7/2002 | Mather et al. |

(Continued)

FOREIGN PATENT DOCUMENTS

| EP | 1202775 B1 | 9/2006 |
| GB | 1439592 | 6/1976 |

(Continued)

OTHER PUBLICATIONS

U.S. Appl. No. 12/512,869, filed Jul. 30, 2009; "Implantable Pressure Sensor with Membrane Bridge"; Arshad A. Alfoqaha.

(Continued)

*Primary Examiner* — Erica Lee
(74) *Attorney, Agent, or Firm* — Michael J. Ostrom

(57) ABSTRACT

This disclosure describes antenna structures for use in an implantable medical device. The implantable medical device may include a housing that hermetically encloses electronic components of the implantable medical device and a fixation mechanism that affixes the implantable medical device to a target location, such as a wall of a vessel. The fixation mechanism functions as a radiating element of an antenna of the implantable medical device. The housing of the implantable medical device may include a conductive loop that electrically couples to a telemetry module and magnetically couples to the fixation mechanism. The telemetry module may provide signals to be transmitted to the inner loop and those signals are magnetically coupled between the inner loop and the fixation mechanism, which radiates the signals.

22 Claims, 5 Drawing Sheets

(56) References Cited

U.S. PATENT DOCUMENTS

| | | | |
|---|---|---|---|
| 6,505,072 B1 | 1/2003 | Linder et al. | |
| 6,561,975 B1 | 5/2003 | Pool et al. | |
| 6,597,926 B1 | 7/2003 | Rek | |
| 6,855,115 B2 | 2/2005 | Fonseca et al. | |
| 6,993,297 B2 | 1/2006 | Smith, Jr. | |
| 7,147,604 B1 | 12/2006 | Allen et al. | |
| 7,245,117 B1 | 7/2007 | Joy et al. | |
| 7,295,879 B2 | 11/2007 | Denker et al. | |
| 7,432,723 B2 | 10/2008 | Ellis et al. | |
| 7,439,723 B2 | 10/2008 | Allen et al. | |
| 7,452,334 B2 | 11/2008 | Gianchandani et al. | |
| 7,466,120 B2 | 12/2008 | Miller et al. | |
| 7,481,771 B2 | 1/2009 | Fonseca et al. | |
| 7,492,144 B2 | 2/2009 | Powers et al. | |
| 7,498,799 B2 | 3/2009 | Allen et al. | |
| 7,532,933 B2 | 5/2009 | Hastings et al. | |
| 7,550,978 B2 | 6/2009 | Joy et al. | |
| 7,574,792 B2 | 8/2009 | O'Brien et al. | |
| 7,591,185 B1 | 9/2009 | Mothilal et al. | |
| 7,595,647 B2 | 9/2009 | Kroh et al. | |
| 7,618,363 B2 | 11/2009 | Yadav et al. | |
| 7,621,036 B2 | 11/2009 | Cros et al. | |
| 7,647,831 B2 | 1/2010 | Corcoran et al. | |
| 7,647,836 B2 | 1/2010 | O'Brien et al. | |
| 7,662,653 B2 | 2/2010 | O'Brien et al. | |
| 7,667,547 B2 | 2/2010 | Ellis | |
| 7,679,355 B2 | 3/2010 | Allen et al. | |
| 7,699,059 B2 | 4/2010 | Fonseca et al. | |
| 7,710,103 B2 | 5/2010 | Powers et al. | |
| 7,748,277 B2 | 7/2010 | O'Brien et al. | |
| 7,829,363 B2 | 11/2010 | You | |
| 7,839,153 B2 | 11/2010 | Joy et al. | |
| 7,854,172 B2 | 12/2010 | O'Brien et al. | |
| 7,909,770 B2 | 3/2011 | Stern et al. | |
| 7,932,732 B2 | 4/2011 | Ellis et al. | |
| 7,936,174 B2 | 5/2011 | Ellis et al. | |
| 7,966,886 B2 | 6/2011 | Corcoran et al. | |
| 7,973,540 B2 | 7/2011 | Kroh et al. | |
| 8,021,307 B2 | 9/2011 | White et al. | |
| 8,026,729 B2 | 9/2011 | Kroh et al. | |
| 8,118,749 B2 | 2/2012 | White et al. | |
| 8,237,451 B2 | 8/2012 | Joy et al. | |
| 8,353,841 B2 | 1/2013 | White et al. | |
| 8,355,777 B2 | 1/2013 | White et al. | |
| 8,360,984 B2 | 1/2013 | Yadav et al. | |
| 8,412,352 B2 | 4/2013 | Griswold et al. | |
| 8,515,559 B2 | 8/2013 | Roberts et al. | |
| 8,669,770 B2 | 3/2014 | Cros | |
| 8,805,505 B1 | 8/2014 | Roberts | |
| 8,870,787 B2 | 10/2014 | Yadav et al. | |
| 8,896,324 B2 | 11/2014 | Kroh et al. | |
| 8,939,905 B2 | 1/2015 | Schugt et al. | |
| 8,942,818 B2 | 1/2015 | Markowitz et al. | |
| 8,983,619 B2 | 3/2015 | Cinbis et al. | |
| 9,078,563 B2 | 7/2015 | Cros et al. | |
| 2002/0003503 A1 | 1/2002 | Justice | |
| 2002/0042637 A1 | 4/2002 | Stover | |
| 2002/0147388 A1 | 10/2002 | Mass | |
| 2003/0105388 A1* | 6/2003 | Roy et al. | 600/300 |
| 2003/0112193 A1 | 6/2003 | Briggs | |
| 2004/0122497 A1* | 6/2004 | Zhang et al. | 607/122 |
| 2004/0127161 A1 | 7/2004 | Leizerovich et al. | |
| 2004/0147969 A1 | 7/2004 | Mann et al. | |
| 2004/0183742 A1 | 9/2004 | Goff et al. | |
| 2004/0212515 A1 | 10/2004 | Eaton et al. | |
| 2005/0001779 A1 | 1/2005 | Copeland et al. | |
| 2005/0065589 A1 | 3/2005 | Schneider et al. | |
| 2005/0065592 A1 | 3/2005 | Holzer | |
| 2005/0187482 A1 | 8/2005 | O'Brien et al. | |
| 2005/0245840 A1 | 11/2005 | Christopherson et al. | |
| 2005/0267550 A1 | 12/2005 | Hess et al. | |
| 2005/0273014 A1 | 12/2005 | Gianchandani et al. | |
| 2006/0161225 A1 | 7/2006 | Sormann et al. | |
| 2006/0174712 A1 | 8/2006 | O'Brien et al. | |
| 2006/0200031 A1 | 9/2006 | White et al. | |
| 2007/0085755 A1 | 4/2007 | Webb et al. | |
| 2007/0091006 A1 | 4/2007 | Thober et al. | |
| 2007/0100385 A1 | 5/2007 | Rawat et al. | |
| 2007/0208403 A1 | 9/2007 | Della Santina et al. | |
| 2007/0229278 A1 | 10/2007 | Nagata et al. | |
| 2007/0270934 A1 | 11/2007 | Stern et al. | |
| 2007/0282210 A1 | 12/2007 | Stern | |
| 2008/0046037 A1 | 2/2008 | Haubrich et al. | |
| 2008/0080452 A1 | 4/2008 | Rofougaran | |
| 2008/0081581 A1 | 4/2008 | Rofougaran | |
| 2008/0081962 A1 | 4/2008 | Miller et al. | |
| 2008/0097567 A1* | 4/2008 | Haldeman | 607/128 |
| 2008/0130194 A1 | 6/2008 | Gray et al. | |
| 2008/0147135 A1 | 6/2008 | Hareland | |
| 2008/0183247 A1 | 7/2008 | Harding | |
| 2008/0204338 A1 | 8/2008 | Rofougaran | |
| 2008/0215117 A1 | 9/2008 | Gross | |
| 2008/0280570 A1 | 11/2008 | Blin | |
| 2008/0288028 A1 | 11/2008 | Larson et al. | |
| 2008/0300658 A1 | 12/2008 | Meskens | |
| 2009/0005656 A1 | 1/2009 | Najafi et al. | |
| 2009/0030291 A1 | 1/2009 | O'Brien et al. | |
| 2009/0141592 A1 | 6/2009 | Huang | |
| 2009/0149825 A1 | 6/2009 | Berland et al. | |
| 2009/0228074 A1 | 9/2009 | Edgell et al. | |
| 2009/0270742 A1 | 10/2009 | Wolinsky et al. | |
| 2009/0270948 A1 | 10/2009 | Nghiem et al. | |
| 2010/0023085 A1* | 1/2010 | Wu et al. | 607/30 |
| 2010/0044444 A1 | 2/2010 | Jain et al. | |
| 2010/0106223 A1 | 4/2010 | Grevious et al. | |
| 2010/0114206 A1 | 5/2010 | Kaemmerer et al. | |
| 2010/0249888 A1 | 9/2010 | Glenn et al. | |
| 2011/0028852 A1 | 2/2011 | Alfoqaha | |
| 2011/0111706 A1 | 5/2011 | Noel | |
| 2011/0126034 A1 | 5/2011 | Siegel et al. | |
| 2012/0001812 A1 | 1/2012 | Zhao et al. | |
| 2012/0029323 A1 | 2/2012 | Zhao | |
| 2012/0064006 A1 | 3/2012 | Yadav | |
| 2012/0109258 A1 | 5/2012 | Cinbis et al. | |
| 2013/0027186 A1 | 1/2013 | Cinbis et al. | |
| 2013/0245469 A1 | 9/2013 | Yadav et al. | |
| 2014/0084943 A1 | 3/2014 | Kroh et al. | |
| 2014/0088994 A1 | 3/2014 | Kroh | |
| 2014/0275861 A1 | 9/2014 | Kroh et al. | |
| 2014/0288085 A1 | 9/2014 | Yadav | |
| 2014/0288459 A1 | 9/2014 | Yadav et al. | |
| 2014/0330143 A1 | 11/2014 | Kroh et al. | |
| 2015/0096167 A1 | 4/2015 | Zhao et al. | |
| 2015/0097734 A1 | 4/2015 | Zhao et al. | |
| 2015/0133796 A1 | 5/2015 | Yadav | |
| 2015/0214604 A1 | 7/2015 | Zhao et al. | |

FOREIGN PATENT DOCUMENTS

| | | |
|---|---|---|
| WO | 0105467 A1 | 1/2001 |
| WO | 2004014456 A2 | 2/2004 |
| WO | 2005067817 A1 | 7/2005 |
| WO | 2005115541 A1 | 12/2005 |
| WO | 2008034077 A2 | 3/2008 |
| WO | 2009055579 A1 | 4/2009 |

OTHER PUBLICATIONS

"Magnetic Loop With Capacitive Load for 30-10M"; http://www.qsl.net/hb9mtn/hb9mtn_adf_loop.html; Retrieved: May 12, 2010.

Office Action from U.S. Appl. No. 12/847,051 dated Sep. 14, 2012 (12 pages).

(PCT/US2011/045919) PCT Notification of Transmittal of the International Search Report and the Written Opinion of the International Searching Authority, Mailed Oct. 28, 2011, 12 pages.

(PCT/US2011/045936) PCT Notification of Transmittal of the International Search Report and the Written Opinion of the International Searching Authority, Mailed Oct. 5, 2011, 11 pages.

Amendment for related U.S. Appl. No. 12/847,051, filed Dec. 13, 2012, (12 pages).

Freudental, et al., "Suitability of NFC for Medical Device Communication and Power Deliver", Engineering in Medicine and Biology Workshop, 2007, IEEE Dallas, vol. 11-12, Nov. 2007, 4 pages.

(56) References Cited

OTHER PUBLICATIONS

Office Action from U.S. Appl. No. 12/847,051, dated Jan. 17, 2014, 16 pp.
Henry Ott Consultants, "Frequency—Wavelength Chart", Feb. 14, 2001, 2 pages.
Office Action from U.S. Appl. No. 12/847,051, dated Oct. 10, 2014, 15 pp.
Office Action from U.S. Appl. No. 13/191,857, dated Oct. 27, 2014, 19 pp.
Response to Office Action dated Oct. 10, 2014, from U.S. Appl. No. 12/847,051, filed Jan. 6, 2015, 11 pp.
Response to Office Action dated Oct. 27, 2014 U.S. Appl. No. 13/191,857, filed Jan. 27, 2015, 11 pp.
Office Action from U.S. Appl. No. 12/847,051, dated May 6, 2015, 15 pp.
Final Rejection from U.S. Appl. No. 12/847,051, dated Nov. 6, 2015, 18 pp.
Response to Office Action dated Sep. 11, 2015, from U.S. Appl. No. 13/191,857, filed Dec. 10, 2015, 6 pp.
Office Action from U.S. Appl. No. 13/191,857, dated May 7, 2015, 21 pp.
Response to Office Action dated May 6, 2015, from U.S. Appl. No. 12/847,051, filed Aug. 5, 2015, 10 pp.
Response to Final Office Action dated May 7, 2015, from U.S. Appl. No. 13/191,857, filed Jul. 7, 2015, 11 pp.
Response to Final Office Action dated May 7, 2015, from U.S. Appl. No. 13/191,857, filed Aug. 7, 2015, 11 pp.
Office Action from U.S. Appl. No. 13/191,857 dated Sep. 11, 2015, 20 pp.
Response to the Office Action mailed Nov. 6, 2015, from U.S. Appl. No. 12/847,051, filed Jan. 6, 2016, 11 pp.

\* cited by examiner

ANTENNA FOR AN IMPLANTABLE MEDICAL DEVICE

TECHNICAL FIELD

The disclosure relates generally to implantable medical devices and, in particular, to antennas for implantable medical devices.

BACKGROUND

A wide variety of implantable medical devices (IMDs) that sense one or more parameters of a patient, deliver a therapy to the patient, or both have been clinically implanted or proposed for clinical implantation in patients. An IMD may deliver therapy to or monitor a physiological or biological condition with respect to a variety of organs, nerves, muscles, tissues or vasculatures of the patient, such as the heart, brain, stomach, spinal cord, pelvic floor, or the like. The therapy provided by the IMD may include electrical stimulation therapy, drug delivery therapy or the like.

The IMD may exchange communications with another device. The IMD may exchange communications with another device that is implanted, attached to (e.g., worn by) the patient or otherwise located near the patient, or remote from the patient. The information exchanged may be information related to a condition of the patient, such as physiological signals measured by one or more sensors, or information related to a therapy delivered to the patient. The IMD may also receive information from the other device, such as information that may be used to control or configure a therapy to be provided to the patient. The IMD and the body worn device may exchange information using any of a variety of communication techniques, including inductive telemetry, magnetic telemetry, radio frequency (RF) telemetry or the like.

SUMMARY

This disclosure describes an antenna for an implantable medical device for wirelessly communicating with another device. As one example, the implantable medical device may be an implantable sensor for continuously monitoring a pressure within a vasculature of the patient. However, the techniques described in this disclosure are applicable to any implantable medical device that measure any of a variety of parameters of the patient, provides a therapy to the patient or both.

The implantable sensor may include a housing that hermetically encloses electronic components of the implantable sensor. The implantable sensor also includes a fixation mechanism that affixes the implantable sensor to the target location, such as a wall of a vessel of the patient. In one particular example, the fixation mechanism may have a generally tubular or cylindrical stent-like shape configured to lodge against a vessel wall when implanted. However, the fixation mechanism may take on any shape. In accordance with the techniques of this disclosure, at least a portion of the fixation mechanism functions as a radiating element of an antenna of the implantable sensor. The housing of the implantable sensor may include a conductive loop that electrically couples to a telemetry module. The telemetry module may provide signals to be transmitted to the conductive loop within the housing and those signals are magnetically coupled between the conductive loop within the housing and the fixation mechanism, which radiates the signals. The conductive loop may be enclosed in a non-conductive header portion of the housing of the implantable sensor to improve the coupling with fixation mechanism.

An antenna structure as described in this disclosure provides a number of advantages. Since the fixation mechanism is typically significantly larger in size than an integrated antenna within the implantable sensor, using the fixation mechanism as a radiating portion of the antenna significantly improves overall radiation efficiency. This, in turn, enables reduced power consumption and/or farther communication range. However, feeding an antenna external to the implantable sensor housing may be challenging. If the fixation mechanism is fed electrically via one or more feed throughs, forces created by pressure within the pulmonary artery or other environment within which the sensor is placed may place mechanical strain at the point of the feed, possibly compromising the feed connection. By magnetically coupling the fixation mechanism to the conductive loop within the housing in accordance with the techniques described herein, the fixation mechanism may function as a radiating portion of the antenna without the need for a feed through to electrically couple the fixation mechanism to the telemetry module within the implantable sensor. Additionally, the structure of the antenna may increase the impedance of the antenna, thus providing a better impedance match with the telemetry module. Other advantages may also be realized by the antenna structure described herein.

In one example, the disclosure is directed to an apparatus comprising a housing and a fixation mechanism mechanically coupled to the housing. The housing includes a telemetry module and a conductive loop that is electrically coupled to the telemetry module. At least a portion of the fixation mechanism is magnetically coupled to the conductive loop to transmit or receive communication signals.

In one example, the disclosure is directed to an apparatus comprising a housing and means for affixing the apparatus to a target location within a patient. The means for affixing is mechanically coupled to the housing. The housing includes a telemetry module and a conductive loop that is electrically coupled to the telemetry module. At least a portion of the means for affixing is magnetically coupled to the conductive loop to transmit or receive communication signals.

In a further example, this disclosure is directed to an apparatus comprising a housing and a cylindrical tubular fixation mechanism that defines a lumen and is mechanically coupled to the housing. The housing includes a telemetry module and a conductive loop that is electrically coupled to the telemetry module. At least a portion of conductive loop is located within the lumen defined by the fixation mechanism and is magnetically coupled to the fixation mechanism.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
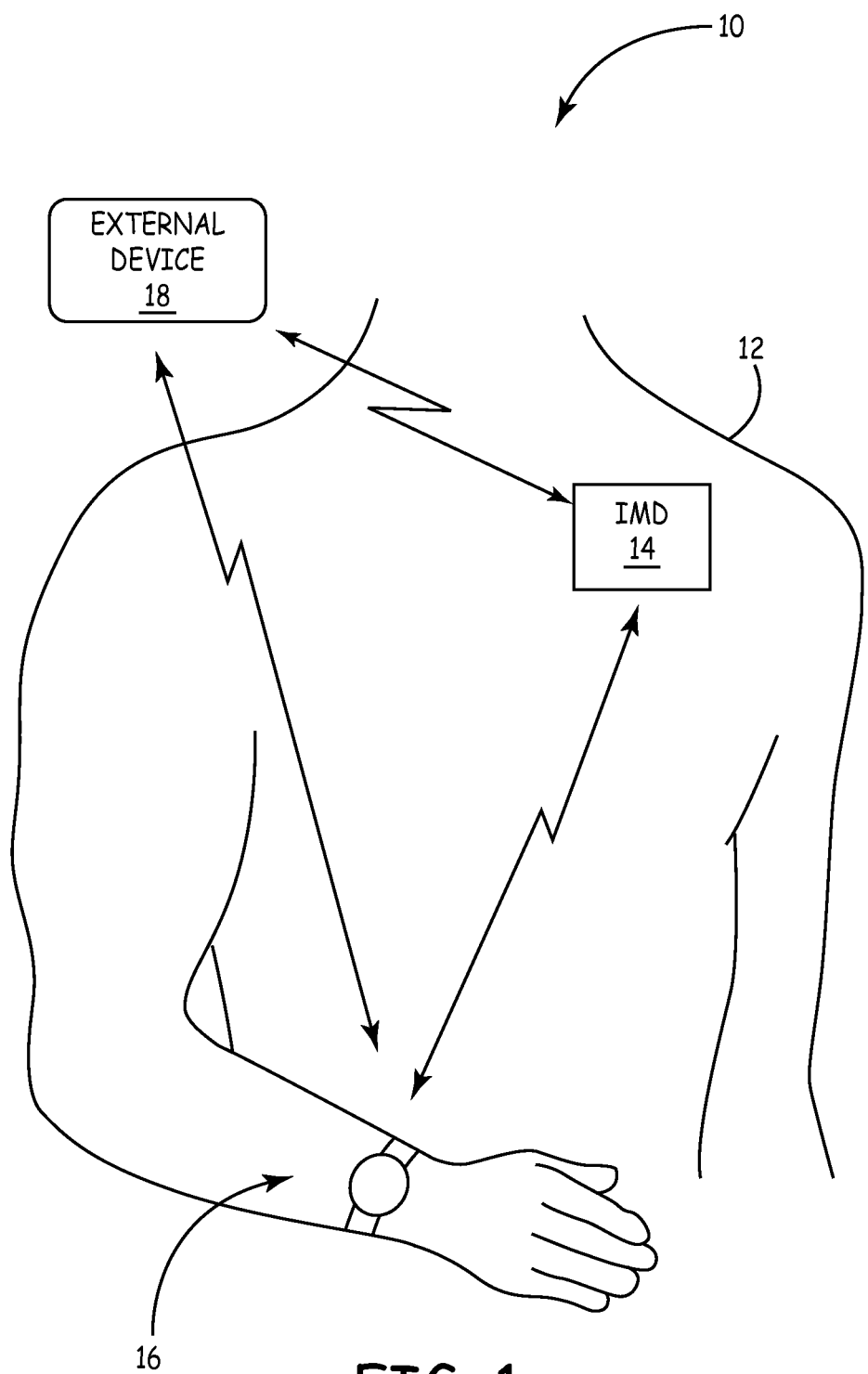
FIG. 1 is a conceptual diagram illustrating an example medical system.

FIG. 1 is a conceptual diagram illustrating an example medical system 10. Medical system 10 includes an implantable medical device (IMD) 14, a body worn device 16 and an external device 18. Medical system 10 may, however, include more of fewer implanted, body worn or external devices. IMD 14, body worn device 16 and external device 18 communicate with one another using any of a number of wireless communication techniques.

IMD 14 may be any of a variety of medical devices that sense one or more parameters of patient 12, provide therapy to patient 12 or a combination thereof. In one example, IMD 14 may be a leadless IMD. In other words, IMD 14 is implanted at a targeted site with no leads extending from the IMD, thus avoiding limitations associated with lead-based devices. Instead, sensing and therapy delivery components are self-contained within IMD 14. In the case of a leadless sensor, IMD 14 includes one or more sensors that measure the parameter(s) of patient 12. In one example, IMD 14 may comprise an implantable pressure sensor placed within a vasculature or chamber of a heart of patient 12. Although this disclosure is described with respect to IMD 14 being an implantable pressure sensor implanted within a heart of patient 12, IMD 14 be placed in locations within patient 12, such as within or proximate to a spinal cord, brain, stomach, or pelvic floor, and may sense, sample, and process any of a variety of parameters such as heart activity, muscle activity, brain electrical activity, intravascular pressure, blood pressure, blood flow, acceleration, displacement, motion, respiration, or blood/tissue chemistry, such as oxygen saturation, carbon dioxide, pH, protein levels, enzyme levels or other parameter or combination of parameters. IMD 14 transmits the sensed parameters to another device, such as body worn device 16, external device 18 or another IMD (not shown in FIG. 1), which may in turn monitor a condition of patient 12 or provide therapy to patient 12 as a function of the sensed parameters.

IMD 14 may provide the therapy to patient 12. IMD 14 may provide the therapy to patient 12 as a function of sensed parameters measured by a sensor of IMD 14 or received from another device, such as another IMD or body worn device 16. As one example, IMD 14 may be a leadless cardiac IMD that provides electrical stimulation therapy (e.g., pacing, cardioversion, defibrillation, and/or cardiac resynchronization) to the heart of patient 12 via one or more electrodes as a function of sensed parameters associated with the heart. In yet a further example, IMD 14 may provide therapy to patient 12 that is not provided as a function of the sensed parameters, such as in the context of neurostimulation. Although described above in the context of electrical stimulation therapy, IMD 14 may provide other therapies to patient 12, such as delivery of a drug or therapeutic agent to patient 12 to reduce or eliminate the condition of the patient and/or one or more symptoms of the condition of the patient, or provide no therapy at all.

Although IMD 14 is described above in the context of a leadless IMD, the techniques described in this disclosure may be utilized in the context of an IMD that is connected to one or more implantable leads (not shown) that include one or more electrodes for delivering therapy to and/or sensing physiological signals of the heart of patient 12. The leads may be implanted at the target tissue site, e.g., within one or more atria or ventricles of the heart of patient 12, within the brain, stomach, pelvic floor, spine or the like.

Body worn device 16 communicates with IMD 14 via wireless communication. Body worn device 16 may communicate with IMD 14 to retrieve information from IMD 14, such as the parameters measured by the one or more sensors of IMD 14 or information related to therapies delivered to patient 12. Body worn device 16 may process the information from IMD 14 to monitor a condition of patient 12. In the case of an implantable pressure sensor, for example, body worn device 16 may receive pressure measurements from IMD 14 and process pressure measurements to monitor for cardiac condition, e.g., heart failure. As another example, body worn device 16 may process sensed cardiac signals to monitor for cardiac condition, e.g., tachycardia. Body worn device 16 may present the information to patient 12 via a display or other user interface and/or relay the information received from IMD 14 to another IMD or to external device 18. Body worn device 16 may also transmit information to IMD 14, such as information identifying a condition of patient 12, information sensed by a sensor of body worn device or another IMD implanted within patient 12, or information received from external device 16. The information transmitted to IMD 14 may, in some instances, control delivery of therapy by IMD 14. Body worn device 16 is illustrated in FIG. 1 as being a watch. However, body worn device 16 may be any of a variety of body worn devices, such as a necklace, armband, belt, ring, bracelet, patch, or other device that is configured to be attached to, worn by, placed on or otherwise coupled to a body of patient 12. Alternatively, body worn device 16 may be a device placed in close proximity to patient 12, such as a cellular telephone, smart phone, pager, personal digital assistant (PDA), or other handheld computing device.

External device 18 may be a programming device or monitoring device that allows a user, e.g., physician, clinician or technician, to configure a therapy delivered by IMD 14 or to retrieve data sensed by IMD 14 or body worn device 16. External device 18 may include a user interface that receives input from the user and/or displays data to the user, thus allowing the user to program the therapy delivered by IMD 14 or display data retrieved from IMD 14 and/or body worn device 16. External device 18 may be a dedicated hardware device with dedicated software for programming or otherwise communicating with IMD 14 and/or body worn device 16. Alternatively, external device 18 may be an off-the-shelf computing device running an application that enables external device 18 to program or otherwise communicate with IMD 14 and/or body worn device 16. In one example, external device 18 may be a computer workstation, such as a CareLink® monitor, available from Medtronic, Inc. of Minneapolis, Minn.

In some instances, IMD 14, body worn device 16 and external device 18 may be communicatively coupled with each other as well as other medical devices (not shown) to form a local area network, sometimes referred to as a body area network (BAN) or personal area network (PAN). Each device may therefore be enabled to communicate wirelessly along multiple pathways with each of the other networked devices. As such, IMD 14, body worn device 16 and external device 18 may represent a distributed system of devices that cooperate to monitor a condition of and/or provide therapy to patient 12. Additionally, one or more of the devices may be coupled to a remote computing device via one or more wired or wireless networks, such as a local area network (LAN), wide area network (WAN), or global network, such as the Internet.

IMD 14, body worn device 16 and external device 18 may communicate with one another by any of a number of wireless communication techniques. In some instances, IMD 14 may communicate with body worn device 16 or external device 18 via inductive telemetry. For example, a physician, technician or other user may place a telemetry head of external device 18, which includes an antenna, near IMD 14 and inductively communicate with IMD 14. In other instances, IMD 14 may communicate with body worn device 16 or external device 18 via RF telemetry. RF telemetry provides communication at further distances than the inductive telemetry such that no telemetry head is needed in the case of RF telemetry.

IMD 14, body worn device 16 and/or external device 18 may communicate in accordance with the Medical Implant Communications Service (MICS) band regulation and/or the Medical External Data Service (MEDS) frequency band regulation. The MICS band regulation defines communication requirements for the 402-405 MHz frequency band. In accordance with the MICS band regulations, the frequency band is divided into ten channels with each channel corresponding to a 300 kilohertz (kHz) sub-band. The MEDS band regulation defines a split channel band with a portion of the MEDS band occupying the 401-402 MHz frequency band and a portion of the MEDS band occupying the 405-406 MHz frequency band. The MEDS band is divided into 20 channels with each channel corresponding to a 100 kHz sub-band, with the first ten channels being located in the 401-402 MHz frequency band and the second ten channels being located in the 405-406 MHz frequency band. The devices of medical system 10 may, however, communicate using any frequency band regulation in addition to or instead of the MICS and MEDS band regulations, such as the industrial, scientific and medical (ISM) frequency bands.

Figure 2:
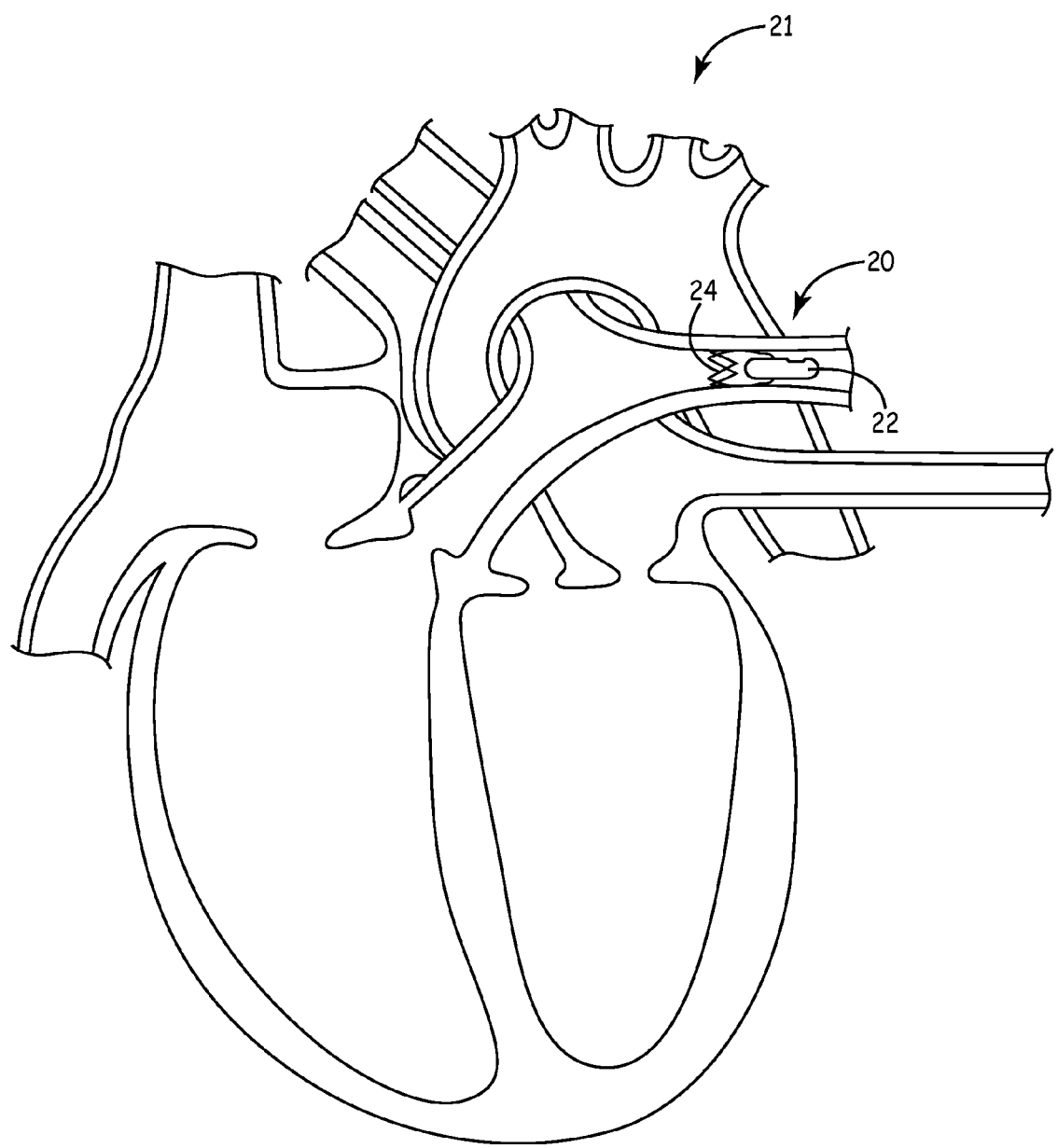
FIG. 2 is a schematic diagram illustrating an example implantable sensor implanted in a heart.

FIG. 2 is a schematic diagram illustrating an example implantable sensor 20 implanted in a heart 21 of a patient 12. Implantable sensor 20 may correspond with IMD 14 of FIG. 1. In the example illustrated in FIG. 2, implantable sensor 20 is implanted in the pulmonary artery (PA) of heart 21. As such, implantable sensor 20 may be sized to be delivered endoluminally using a delivery system tracked through the vasculature from a percutaneous entry site such as a femoral, jugular or subclavian vein or artery, and may have an outer diameter between 16-18 French (5.3-6 mm) However, implantable sensor 20 may be placed within or near other portions of heart 21, such as in one of the chambers (atrial or ventricular), veins, vessels, arteries or other vasculature of heart 21, such as the aorta, renal arteries, or inferior or superior vena cava. In further instances, implantable sensor 20 may be placed on the outside of heart 21 or in locations other than heart 21.

Implantable sensor 20 includes a housing 22 and a fixation mechanism 24. Housing 22 is a capsule-shaped housing that hermetically encloses components of implantable sensor 20, such as at least one sensor, processor, memory, power source, telemetry circuitry, or the like. In one example, housing 22 may include a pressure sensing device that obtains pressure measurements in an environment surrounding housing 22. Thus, implantable sensor 20 may be an active leadless pressure sensor system designed to continuously monitor blood pressure and transmit the pressure measurements to an external device to allow physicians to proactively administer medications so that patients avoid dangerous blood pressure spikes. However, implantable sensor 20 may sense pressure measurements of other locations of heart 21 depending on the location of implantation. In other examples, housing 22 may house sensor(s) for obtaining measurements of other parameters, such as heart activity, muscle activity, brain electrical activity, blood flow, acceleration, displacement, motion, respiration, or blood/tissue chemistry, such as oxygen saturation, carbon dioxide, pH, protein levels, enzyme levels or other parameter or combination of parameters.

Fixation mechanism 24 affixes implantable sensor 20 to the target location, such as the wall of the pulmonary artery in the example illustrated in FIG. 2. Fixation mechanism 24 of FIG. 2 is a generally tubular or cylindrical stent-like structure that is configured to lodge against a vessel wall when implanted. In one embodiment, fixation mechanism 24 is mechanically coupled to housing 22 such that implantable sensor 20 is substantially radially centered within vasculature when implanted. In other embodiments, fixation mechanism 24 may be mechanically coupled to housing 22 such that implantable sensor 20 is adjacent to the wall of the vasculature when implanted. Although illustrated as a stent-like fixation mechanism, fixation mechanism 24 may be a different fixation mechanism that exerts enough force against, embeds within, extends through or otherwise affixes implantable sensor 20 to the target location.

As will be described in further detail below, implantable sensor 20 transmits and receives wireless signals via an antenna. In accordance with the techniques of this disclosure, fixation mechanism 24 functions as part of the antenna of implantable sensor 20. In particular, telemetric signals are magnetically coupled between fixation mechanism 24 and a conductive loop (not shown in FIG. 2) within housing 22. Since the fixation mechanism is typically significantly larger in size than an integrated antenna within the implantable sensor, using the fixation mechanism as a radiating portion of the antenna significantly improves overall radiation efficiency. This, in turn, enables reduced power consumption and/or farther communication range. By magnetically coupling signals to fixation mechanism 24, fixation mechanism 24 may function as an antenna without the need for a feed through to electrically couple fixation mechanism 24 to telemetry circuitry within implantable sensor 20.

Figure 3:
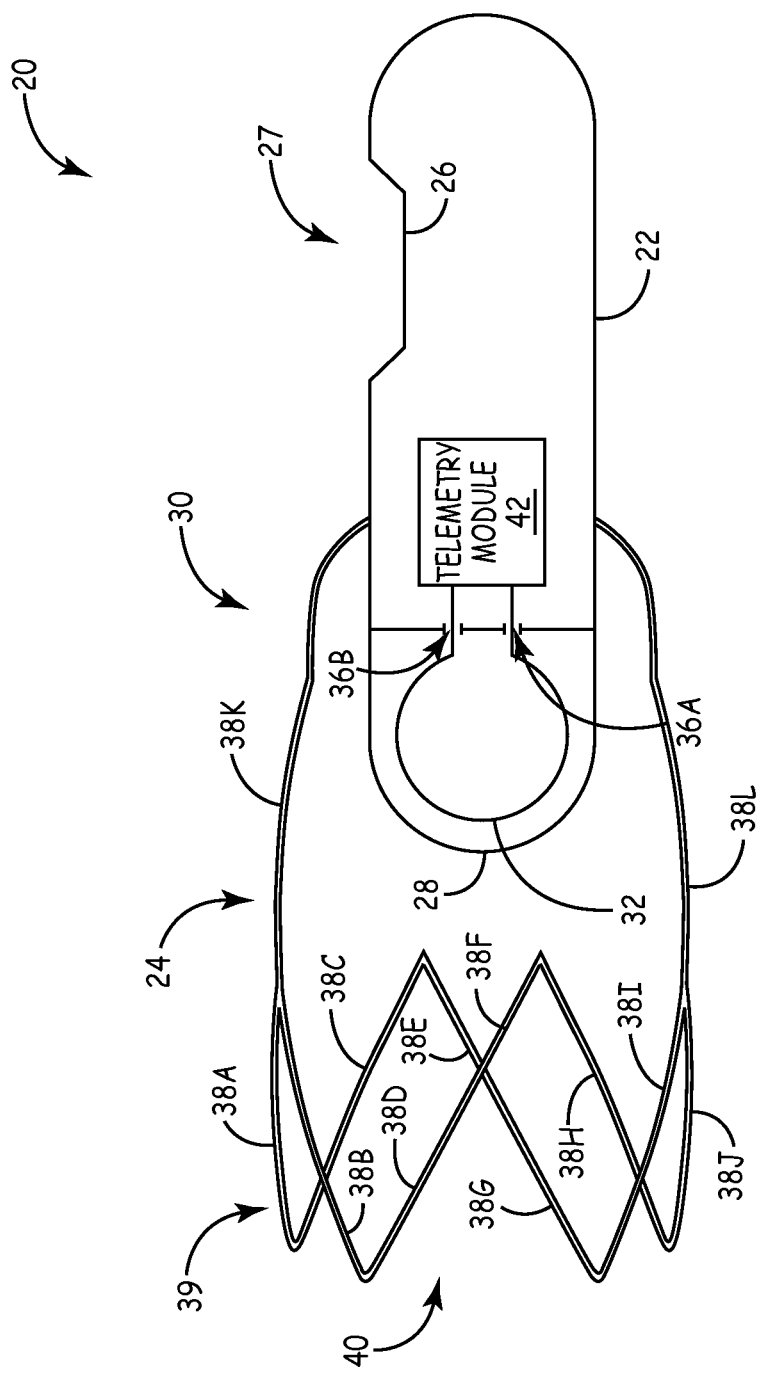
FIG. 3 is a schematic diagram illustrating the implantable sensor of FIG. 2 in further detail.

FIG. 3 is a schematic diagram illustrating implantable sensor 20 in further detail. As described above, housing 22 hermetically encloses components of implantable sensor 20, such as at least one sensor, processor, memory, power supply, telemetry circuitry, or the like. Housing 22 of FIG. 3 has a long, thin cylindrical shape (e.g., capsule-like shape) to accommodate placement in the pulmonary artery of heart 21 (as illustrated in FIG. 2). Housing 22 may have a different shape depending on the location desired for implantation, type of sensor, or the like. For example, housing 22 may be formed in a different shape to accommodate placement within a chamber of heart 21, along a spine, in a brain, or other location within or on patient 12. Therefore, the techniques described in this disclosure should not be limited by the shape of housing 22 described herein.

Housing 22 may be formed of any of a variety of materials including conductive materials, non-conductive materials, or a combination thereof. Examples of a biocompatible, conductive material includes titanium, stainless steel, MP35N alloy (a nonmagnetic, nickel-cobalt-chromium-molybdenum alloy), or platinum or the like. Examples of a biocompatible, non-conductive materials include silicone rubber, polyurethane, epoxy, acetyl co-polymer plastics, PolyEtherEtherKetone (PEEK), liquid crystal polymer (LCP) plastics, or the like.

Housing 22 is formed to have an opening 27 that exposes pressure sensing device 26 to the environment at the target location. In the example illustrated in FIG. 3, opening 27 of housing 22 is located along a length of housing 22. However, in other embodiments, opening 27 of housing 22 may be located on either end of housing 22. In any case, pressure sensing device 26 is exposed to the surrounding environment to obtain pressure measurements of the surrounding environment.

Pressure sensing device 26 may include a deformable diaphragm that moves in response to changes in the pressure of the environment to which it is exposed. Accordingly, there is a direct relationship between the movement of the diaphragm and the change in pressure. The diaphragm of pressure sensing device 26 may be positioned adjacent to opening 27 of housing 22 so that pressure from the surrounding environment will act upon the diaphragm through opening 27 of housing 22. It is understood that in accordance with one or more embodiments, the diaphragm may be a component of a capacitor structure used in generating capacitive measurements indicative of the pressure of the surrounding environment. In other words, pressure exerted on the diaphragm causes a corresponding movement of diaphragm which in turn alters a measured capacitance. As such, the measured capacitance corresponds to the pressure from the surrounding environment acting on the diaphragm. By way of example only and without limitation, pressure sensing device 26 may comprise a pressure sensor constructed in a manner similar to that described in commonly assigned U.S. Pat. No. 6,221,024, entitled "Implantable Pressure Sensor and Method of Fabrication," U.S. patent application Ser. No. 12/512,869 filed Jul. 30, 2009 and entitled "Implantable Pressure Sensor with Membrane Bridge," and U.S. Pat. No. 7,591,185, entitled "Pressure Sensor Configurations for Implantable Medical Electrical Leads" the contents of each of which are hereby incorporated by reference for their description of pressure sensors.

Although described above as a capacitive pressure sensor, pressure sensing device 26 may be any sort of pressure sensing device, such as an electromagnetic pressure sensor that measures displacement of the diaphragm by means of changes in inductance (reluctance), linear variable differential transformer (LVDT), Hall Effect or eddy currents, a piezoelectric pressure sensor, optical pressure sensor, or any other pressure sensor. Housing 22 may include other types of sensors instead of or in addition to pressure sensing device 26, such as pH sensor, oxygen sensor, temperature sensor, electrode, or any other type of sensor.

Housing 22 is mechanically coupled to fixation mechanism 24 that affixes implantable sensor 20 to the target location within patient 12. Fixation mechanism 24 may be mechanically coupled to housing 22 via spot welding, adhesive or other coupling mechanism. As described above, fixation mechanism 24 is a generally tubular or cylindrical stent-like structure that is configured to lodge against a vessel wall when implanted to hold implantable sensor 20 at the target location. Fixation mechanism 24 includes a plurality of struts 38A-38L that are arranged to form fixation mechanism 24. In particular, struts 38A-38J are arranged to form a ring 39 having a lumen 40. In the example illustrated in FIG. 3, struts 38A-38J form a zig-zag shaped ring 39. However, struts 38A-38J may be arranged to form a ring of a different shape, such as a sinusoidal shaped ring. Struts 38K and 38L mechanically couple on one end to ring 39 and on the opposite end to housing 22 to attach fixation mechanism 24 to housing 22.

Struts 38A-38L may be made from a variety conductive materials suitable for implantation, including, but not limited to, nickel-titanium (nitinol), stainless steel, tantalum, nickel, titanium, nickel-cobalt-chromium-molybdenum "superalloy," combinations of the above, and the like. In some embodiments, a portion of struts 38A-38L may be made of one or more the conductive materials described above while the other portions of struts 38A-38L may be made of non-conductive materials, such as polymeric materials. In this case, the conductive path of fixation mechanism 24 may be specifically designed to obtain a particular radiation pattern. The material from which struts 38A-38L are made may be capable of being manipulated such that fixation mechanism 24 may be radially compressed or otherwise manipulated to aid in delivery of implantable sensor 20 to the target location. When located at the target location, fixation mechanism may be expanded in situ, e.g., via inflation of a balloon (not shown), such that at least a portion of struts 38 securely engage the vessel wall.

Fixation mechanism 24 is illustrated in FIG. 3 as including a single ring 112, fixation mechanism 24 may include a plurality of rings joined in series to form the cylindrical tubular body of various lengths. The number of rings may depend upon the desired length of fixation mechanism 24. For example when the target implantation site is relatively short, it would be desirable for fixation mechanism 24 to have a smaller number of rings. Moreover, although illustrated as a stent-like fixation mechanism, fixation mechanism 24 may be a different fixation mechanism that exerts enough force against, embeds within, extends through or otherwise affixes implantable sensor 20 to the target location. For example, implantable sensor 20 may include one or more tines, loops, or other mechanism that may be used to affix implantable sensor 20 to the target location.

As described above with respect to FIG. 2, implantable sensor 20 communicates with one or more other devices, such as external device 18, body worn device 16 or another implantable medical device. To this end, implantable sensor 20 includes an antenna 30 to transmit and receive signals from the one or more other devices. As described in detail herein, antenna 30 includes an inner portion and an outer portion. A conductive loop 32 within housing 22 may function as the inner portion of antenna 30 and at least a portion of fixation mechanism 24 may function as the outer portion of antenna 30. Fixation mechanism 24 (or a portion of fixation mechanism 24) may therefore function as an outer conductive "loop" of antenna 30.

In one embodiment, housing 22 may include a header portion 28 that includes conductive loop 32 of antenna 30. Header portion 28 may be formed of a non-conductive, biocompatible material. Header portion 28 includes a mounting surface that conforms to and is mechanically affixed against a mating sidewall surface housing 22. When housing 22 is formed from a non-conductive material, implantable sensor 20 may not include a header portion 28. Instead, the conductive loop 32 may be located within housing 22.

Header portion 28 includes one or more electrical interconnects (such as feed through pins) that electrically connect conductive loop 32 of antenna 30 to a telemetry module 42 within housing 22. The telemetry module feeds signals to and receives signals from conductive loop 32 via feed ports 36. Fixation mechanism 24 (or at least a portion of fixation mechanism 24) is magnetically coupled to conductive loop 32. In other words, a change in current flow through conductive loop 32 (e.g., due to a signal received from the telemetry module) generates a magnetic field that induces a current in fixation mechanism 24 thus coupling the energy to fixation mechanism 24. Likewise, a change in current flow through fixation mechanism 24 (e.g., due to a signal received from another device) generates a magnetic field that induces a current in conductive loop 32 thus coupling the energy.

Conductive loop 32 and fixation mechanism 24 are located in close proximity to one another to achieve the magnetic coupling. In some embodiments, at least a portion of housing 22 of implantable sensor 20 is located within lumen 40 defined by fixation mechanism 24. The diameter of lumen 40 is greater than the diameter of housing 22 such that the portion of housing 22 may fit within lumen 40. In the example illustrated in FIG. 3, header portion 28 is located within the portion of lumen 40 defined by struts 38K and 38L. In other embodiments, more or less of housing 22 may be located within lumen 40. For example, header portion 28 of housing 22 may be located within the portion of lumen defined by ring 39 or additional rings connected in series with ring 39. Not only does disposing at least a portion of housing 22 within lumen 40 increase the magnetic coupling, the overall length of implantable sensor 20 is reduced, which may be particularly advantageous when implantable sensor 20 is implanted at an target site having a relatively short landing zone within the vessel.

The structure of antenna 30 illustrated in FIG. 3 provides a number of advantages. As one example, using fixation mechanism 24 as a radiating portion of antenna 30 significantly improves overall radiation efficiency since fixation mechanism 24 is typically significantly larger in size than an integrated antenna within the implantable sensor. This, in turn, enables reduced power consumption and/or farther communication range. As another example, the dual loop structure of antenna 30 allows fixation mechanism 24 to be used as a radiating portion of antenna 30 without requiring that fixation mechanism 24 being electrically coupled to telemetry module 42. In other words, the antenna structure of antenna 30 eliminates the need for a feed through to which fixation mechanism 24 is coupled. Forces created by pressure within the pulmonary artery or other environment within which implantable sensor 20 is placed may put mechanical strain at the point of the feed, possibly compromising the feed connection. Mechanically coupling energy to fixation mechanism 24 without electrical feed throughs eliminates this potential problem. Additionally, the structure of antenna 30 may increase the impedance of antenna 30, thus providing a better impedance match with telemetry module 42 (e.g., close to 50 Ohms), which again may improve overall radiation efficiency.

Conductive loop 32 may include one or more turns of a conductive material. In the example illustrated in FIG. 3, conductive loop 32 has a circular shape. However, conductive loop 32 may be formed in any of a variety of shapes, including square, rectangle, triangle, oval or any other shape. In some instances, the shape of conductive loop 32 may be dependent on a size and shape of header portion 28 and/or housing 22 of implantable sensor 20. The sizes of conductive loop 32 may depend on the size and shape of header portion 28 and/or housing 22 of implantable sensor 20, the frequency at which communication occurs, the location at which implantable sensor 20 is implanted or the like. In one example, conductive loop 32 can be a small fraction of the wavelength, such as less than or equal to approximately one twentieth ($1/20$) of a wavelength at 400 MHz in human tissue (e.g., approximately 5 mm), and the circumference of fixation mechanism 24 may be from a fraction (e.g., one-third ($1/3$)) to one wavelength at 400 MHz in human tissue (e.g., approximately 3.2 cm to 9.6 cm). As such, the antenna configuration described in this disclosure may provide a small footprint within implantable sensor 20 while still maintaining high radiation efficiency.

In the example illustrated in FIG. 3, the portion of housing 22 enclosing conductive loop 32 (e.g., header portion 28) is located within at least a portion of lumen 40 defined by fixation mechanism 24. However, header portion 28 may be located outside of lumen 40 as long as there is sufficient magnetic coupling between conductive loop 32 and fixation mechanism 24 to couple the signals between the two structures. Additionally, conductive loop 32 and fixation mechanism 24 may be coplanar or non-coplanar, coaxial or non-coaxial, collinear or non-collinear, or any combination thereof. Conductive loop 32 and fixation mechanism 24 may in one example be located in parallel planes. In other embodiments, conductive loop 32 and fixation mechanism 24 may be located in different planes that are not parallel with one another, but are oriented such that there is sufficient magnetic coupling between conductive loop 32 and fixation mechanism 24.

The antenna structure illustrated in FIG. 3 is one example structure in accordance with this disclosure. However, the antenna structure of FIG. 3 should not be considered limiting of the techniques described herein. For instance, the techniques of this disclosure may be used with any fixation mechanism (e.g., ones having different mechanical structures) for which there is sufficient magnetic coupling between the fixation mechanism and the inner feed loop. For example, the fixation mechanism may have open ends instead of being a "closed" loop. As another example, the fixation mechanism (whether closed loop or open loop) may include one or more lumped capacitive elements depending on the length of the fixation mechanism to adjust the resonance frequency and/or impedance.

Moreover, the techniques may further be applicable beyond the use of a fixation mechanism. For example, conductive loop 32 may magnetically couple to a conductive loop that does not dually function as a fixation mechanism. As another example, conductive loop 32 may magnetically couple to a portion of housing 22 of implantable sensor 20 thus using housing 22 as a radiating element of antenna 30.

Figure 4:
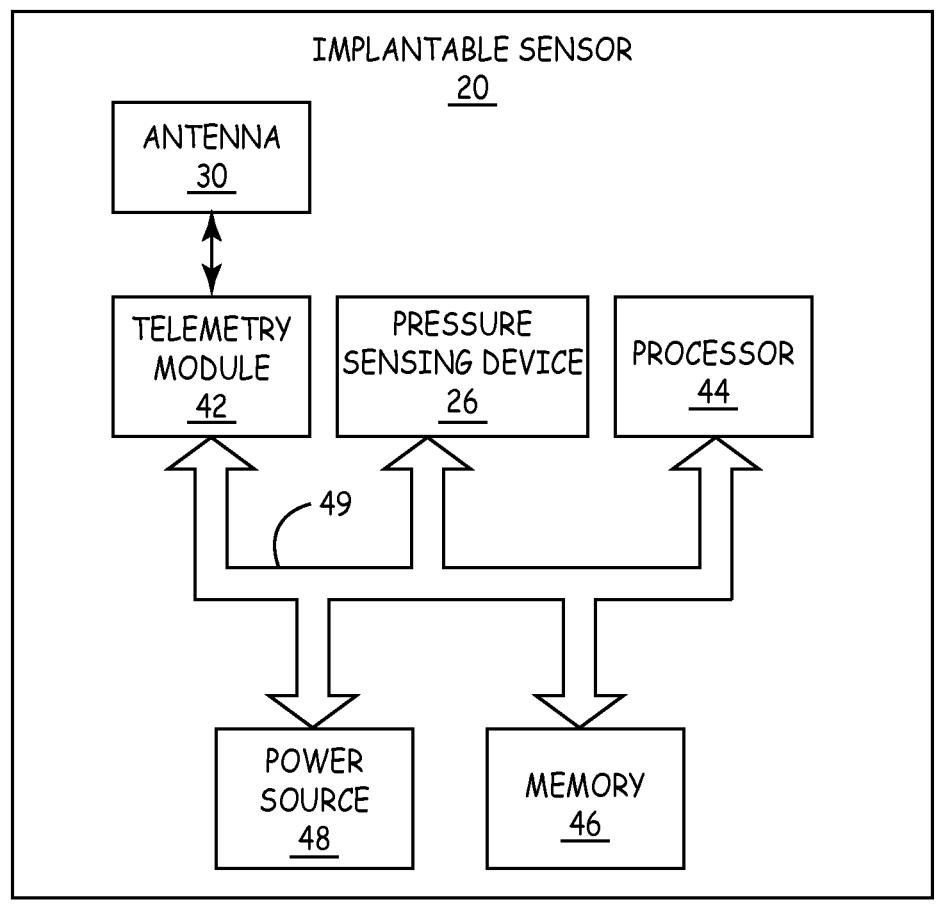
FIG. 4 is a block diagram illustrating components of an implantable sensor.

FIG. 4 is a block diagram illustrating components of implantable sensor 20 in further detail. Implantable sensor 20 includes a pressure sensing device 26, antenna 30, telemetry module 42, processor 44, memory 46 and power source 48. The components of implantable sensor 20 are shown to be interconnected by a data/communication bus 49, but may be interconnected by other means including direct electrical or non-electrical connections or a combination of different types of connections.

As described above, implantable sensor 20 may sense one or more parameters (e.g., physiological or biological parameters) of patient 12 and/or detect one or more conditions from the sensed parameters. As describe above with respect to FIG. 3, for example, pressure sensing device 26 is configured to obtain signals related to the pressure of the surrounding environment within which implantable sensor 20 is placed. Although described with respect to implantable sensor including pressure sensing device 26, implantable sensor 20 may include other types of sensors instead of or in addition to pressure sensing device 26, such as pH sensor, oxygen sensor, temperature sensor, electrodes, or any other type of sensor.

The parameters sensed by pressure sensing device 26 may be stored in memory 46. In some instances, the sensed parameters may be stored in raw form. In other instances, the sensed parameters may be processed and the processed parameters may be stored in memory 46. For example, implantable sensor 20 may include one or more analog or digital components that amplify and filter the sensed parameters and store the filtered parameters in memory 46. The parameters stored in memory 46 may, in some cases, be retrieved and further processed by processor 44. Processor 44 may, for example, process the sensed parameters to monitor or detect a condition of patient 12.

Processor 44 controls telemetry module 42 to transmit communications to and/or receive communications from another medical device, such as body worn device 16, external device 18, or another implanted medical device. As such, telemetry module 42 may include one or more transceivers or, in instances in which implantable sensor 20 only supports unidirectional communication, one or more transmitters or one or more receivers. In some instances, telemetry module 42 may include two or more sets of components, e.g., one for inductive communication and one for RF communication. As described in detail above, antenna 30 is formed from a conductive loop 32 within housing 22 and at least a portion of fixation mechanism 24.

Processor 44 may provide the data to be transmitted and control signals for transmit and receive circuitry within telemetry module 42, e.g., via data bus 49. Telemetry module 42 transmits the data to another device (e.g., body worn device 16, external device 18, or another implanted device) in accordance with the control signals from processor 44. Telemetry module 42 may also provide data received from another device to processor 44 in the case of incoming communications. Processor 44 may analyze the received data, store the received data within memory 46 and configure components of implantable sensor 20 in accordance with the received data.

Telemetry module 42 includes any suitable hardware, firmware, software or any combination thereof for communicating with another device. For example, telemetry module 42 may include appropriate modulation, demodulation, frequency conversion, filtering, amplifier or other components for transmission and reception of data. Telemetry module 42 is also coupled to an antenna 30, such as any of the antenna configurations described herein, for transmitting and receiving signals.

Power source 48 may include a rechargeable or non-rechargeable battery. A non-rechargeable battery may be selected to last for several years, while a rechargeable battery may be charged from an external charging device on an as-need basis, e.g., daily or weekly basis. In either case, and especially in the case of the non-rechargeable battery, the amount of power of the battery is limited. As such, it is desirable to reduce the amount of power drained from power source 48 as much as possible.

Implantable sensor 20 of FIG. 4 is provided for purposes of illustration. Implantable sensor 20 may include more or fewer components than those illustrated in FIG. 4. For example, implantable sensor 20 may be an implantable medical device configured to also provide therapy, such as electrical stimulation therapy or drug delivery therapy, in accordance with parameters of one or more selected therapy programs. In this case, implantable sensor may include a therapy module (not shown) to generate therapy according to one or more therapy programs. In the case of electrical stimulation therapy, the therapy module may include a stimulation generator that generates and delivers electrical stimulation therapy, e.g., in the form of pulses or shocks, via one or more electrodes on housing 22, header 28 or a lead extending from the implantable medical device. Processor 44 may control the stimulation generator to deliver electrical stimulation pulses with amplitudes, pulse widths, frequency, and/or electrode polarities specified by the one or more therapy programs. In the case of drug delivery therapy, the therapy module may include a pump that delivers a drug or therapeutic agent, e.g., via a catheter or other delivery mechanism. Processor 44 may control the pump to deliver the drug or therapeutic agent with the dosage and frequency (or rate) specified by the one or more therapy programs. As such, the techniques of this disclosure should not be considered limited to the example described in FIG. 4.

Figure 5:
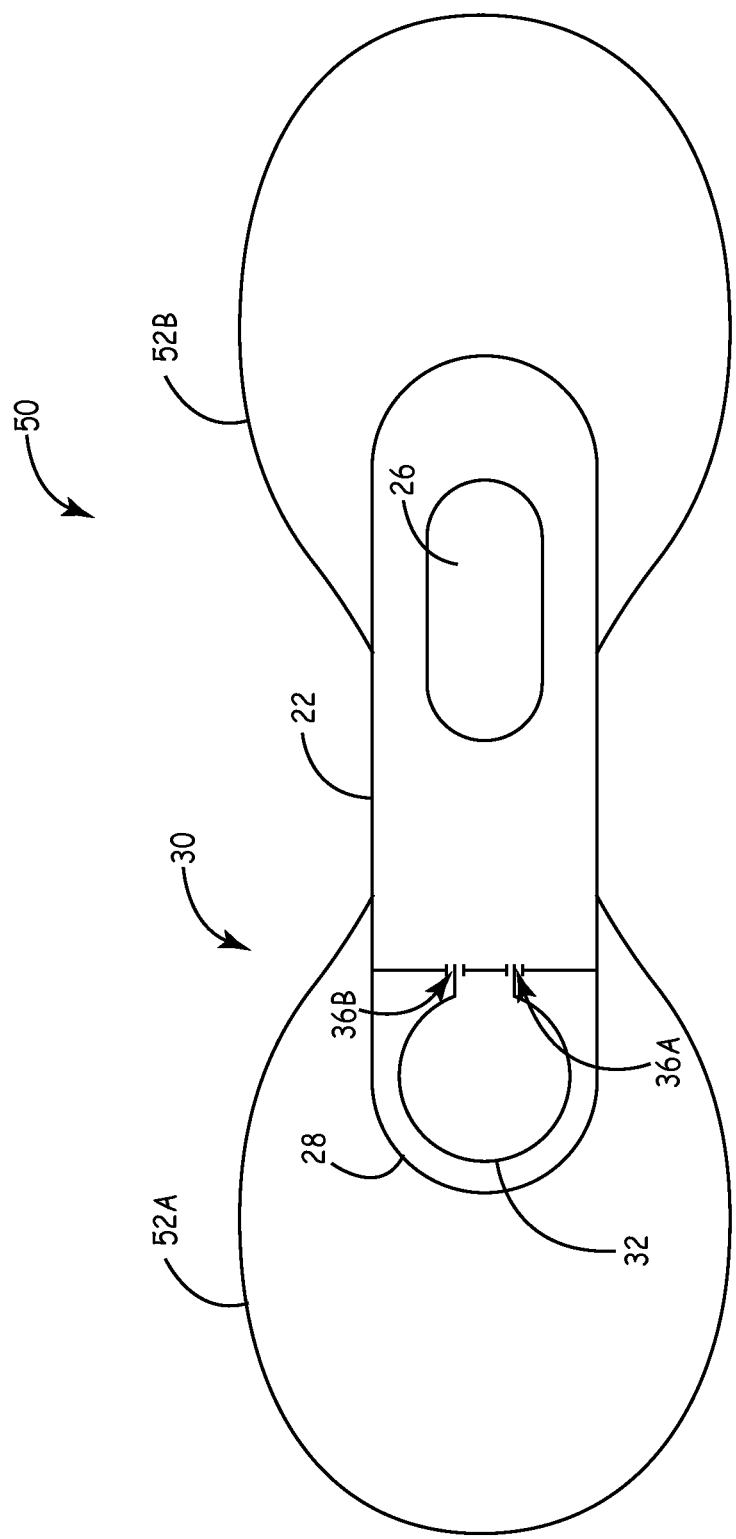
FIG. 5 is a schematic diagram illustrating another example implantable sensor.

FIG. 5 is a schematic diagram illustrating another example implantable sensor 50. Implantable sensor 50 conforms substantially to implantable sensor 20 of FIG. 3, but has a different fixation mechanism. In particular, implantable sensor 50 includes fixation loops 52A and 52B (collectively, "fixation loops 52") that form the fixation mechanism of implantable sensor 50. Loops 52 may be formed of a conductive material, such as a conductive wire. Loops 52 affix implantable sensor 50 within the vasculature due to force applied to the vessel wall by the respective loops 52A and 52B opening radially against the vessel. Although illustrated in FIG. 5 as including two fixation loops 52, implantable sensor 50 may include only a single fixation loop (e.g., only loop 52A) or more than two fixation loops.

Loop 52A of implantable sensor 50 magnetically couples to conductive loop 32 within housing 22 to function as a radiating member of antenna 30 in a manner similar to fixation element 24 described above with respect to FIG. 3. In the example illustrated in FIG. 5, conductive loop 32 and fixation loop 52A have a circular shape and oval shape, respectively, with conductive loop 32 positioned at least partially within the circumference of fixation loop 52A. However, conductive loop 32 and fixation loop 52A may be formed in any of a variety of shapes, including square, rectangle, triangle, oval or any other shape. In some instances, the shape of conductive loop 32 may be dependent on a size and shape of header portion 28 and/or housing 22 of implantable sensor 20. The sizes of conductive loop 32 may depend on the size and shape of header portion 28 and/or housing 22 of implantable sensor 20, the frequency at which communication occurs, or the like. The size and shape of fixation loops 52 may depend on the target location of implantation of implantable sensor 20. In one example, conductive loop 32 can be a small fraction of the wavelength, such as less than or equal to approximately one twentieth (1/20) of a wavelength at 400 MHz in human tissue (e.g., approximately 5 mm), and the circumference of fixation mechanism 24 may be from a fraction (e.g., one-third (1/3)) to one wavelength at 400 MHz in human tissue (e.g., approximately 3.2 cm to 9.6 cm).

In the example illustrated in FIG. 3, conductive loop 32 within housing 22 is positioned at least partially within the circumference of fixation loop 52A. However, a portion or all of conductive loop 32 may be located outside of the circumference of fixation loop 52A as long as there is sufficient magnetic coupling between conductive loop 32 and fixation loop 52A to couple the signals between the two structures. Additionally, conductive loop 32 and fixation loop 52A may be coplanar or non-coplanar, coaxial or non-coaxial, collinear or non-collinear, or any combination thereof. Conductive loop 32 and fixation loop 52A may in one example be located in parallel planes, but not coplanar. In other embodiments, conductive loop 32 and fixation loop 52A may be located in different planes that are not parallel with one another, but are oriented such that there is sufficient magnetic coupling between conductive loop 32 and fixation loop 52A. Moreover, in some instances, fixation loops 52A and 52B may be formed from a single conductive wire that is shaped into a figure eight and attached to housing 22 at a common point. In this manner, both of fixation loops 52 may function as radiating portions of the antenna.

The techniques described in this disclosure may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing circuitry, alone or in combination with other circuitry, or any other equivalent circuitry.

Such hardware, software, or firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These examples, however, should not be considered limiting of the techniques described in this disclosure. For instance, the techniques of this disclosure may be used with any fixation mechanism for which there is sufficient magnetic coupling between the fixation mechanism and the inner feed loop. Moreover, the techniques may further be applicable beyond the use of a fixation mechanism. For example, the inner loop may magnetically couple to a portion of the housing of the implantable medical device thus using the implantable medical device housing as a radiating element of the antenna. In yet another example, the inner loop may on a chip and magnetically couple to a planar loop around the chip. As a further example, the outer conductive potion may be other structures with open ends rather than a closed loop. These and other examples are within the scope of the following claims.

The invention claimed is:

1. An apparatus comprising:
 a housing that includes:
  a telemetry module; and
  an inner conductive feed loop that is electrically coupled to the telemetry module, wherein at least a portion of the inner conductive feed loop forms a portion of an antenna; and
 a fixation mechanism located outside the housing and mechanically coupled to the housing, and configured to affix the apparatus to a target location, wherein at least a portion of the fixation mechanism forms a radiating portion of the antenna, the fixation mechanism being magnetically coupled through the housing to the conductive feed loop to obtain the communication signals to be transmitted by the telemetry module and radiate the signals from the telemetry module to another device.

2. The apparatus of claim 1, wherein the fixation mechanism is a cylindrical stent-like structure that is configured to lodge against a vessel wall.

3. The apparatus of claim 1, wherein the fixation mechanism includes a plurality of struts arranged to form the fixation mechanism, wherein a first portion of the plurality of struts form a ring and a second portion of the plurality of struts mechanically couple the ring to the housing.

4. The apparatus of claim 3, wherein the first portion of the plurality of struts form a ring having one of a zig-zag shape and a sinusoidal shape.

5. The apparatus of claim 1, wherein the fixation mechanism includes a plurality of struts arranged to form the fixation mechanism, wherein a first portion of the plurality of struts form a plurality of rings that are joined in series to form the cylindrical body and a second portion of the plurality of struts mechanically couple the cylindrical body to the housing.

6. The apparatus of claim 1, wherein the fixation mechanism includes at least one fixation loop mechanically coupled to the housing.

7. The apparatus of claim 6, wherein at least a portion of the conductive loop within the housing is located within the circumference of the fixation loop.

8. The apparatus of claim 1, wherein a shape of the fixation mechanism defines a lumen and at least a portion of the conductive loop is located within the lumen defined by the fixation mechanism.

9. The apparatus of claim 8, wherein the entire housing is located within the lumen defined by the fixation mechanism.

10. The apparatus of claim 1, further comprising a sensor within the housing to measure one or more parameters.

11. The apparatus of claim 1, wherein the sensor comprises one of a pressure sensor, a pH sensor, an oxygen sensor, a temperature sensor, and an electrode.

12. The apparatus of claim 1, wherein the housing further includes:
 a non-conductive header portion that includes the conductive loop;
 a feed through via which the conductive loop is electrically coupled to the telemetry module.

13. An apparatus comprising:
 a housing that includes:
  a telemetry module; and
  an inner conductive feed loop that is electrically coupled to the telemetry module, wherein at least a portion of the inner conductive feed loop forms a portion of an antenna; and
 means for affixing the apparatus to a target location within a patient, wherein the means for affixing is located outside the housing and mechanically coupled to the housing and at least a portion of the means for affixing forms a radiating portion of the antenna, the means for affixing being magnetically coupled to the conductive feed loop through the housing to obtain the communication signals to be transmitted by the telemetry module and radiate the signals from the telemetry module to another device.

14. The apparatus of claim 13, wherein the means for affixing the apparatus to the target location is a cylindrical stent-like structure.

15. The apparatus of claim 13, wherein the means for affixing includes a plurality of struts, wherein a first portion of the plurality of struts form a ring and a second portion of the plurality of struts mechanically couple the ring to the housing.

16. The apparatus of claim 13, wherein the means for affixing includes a plurality of struts, wherein a first portion of the plurality of struts form a plurality of rings that are joined in series to form the cylindrical body and a second portion of the plurality of struts mechanically couple the cylindrical body to the housing.

17. The apparatus of claim 13, wherein the means for affixing the fixation mechanism includes at least one fixation loop mechanically coupled to the housing.

18. The apparatus of claim 13, wherein at least a portion of the conductive loop within the housing is located within a circumference of the means for affixing.

19. The apparatus of claim 13, wherein the means for affixing defines a lumen and at least a portion of the conductive loop is located within the lumen defined by the fixation mechanism.

20. An apparatus comprising:
a housing that includes:
  a telemetry module; and
  a conductive feed loop that is electrically coupled to the telemetry module; and
a cylindrical fixation mechanism that defines a lumen and is mechanically coupled to the housing, wherein the cylindrical fixation mechanism forms a radiating portion of an antenna,
  wherein at least a portion of conductive feed loop is located within the lumen defined by the cylindrical fixation mechanism and is magnetically coupled to the cylindrical fixation mechanism such that the at least a portion of the conductive feed loop is configured to provide communication signals to be radiated from the telemetry module to the cylindrical fixation mechanism,
  further wherein the cylindrical fixation mechanism radiates the signals from the telemetry module to another device.

21. The apparatus of claim 20, wherein the entire housing is located within the lumen defined by the cylindrical fixation mechanism.

22. The apparatus of claim 20, wherein the conductive loop within the housing is less than or equal to approximately 5 millimeters (mm) and a circumference of the cylindrical fixation mechanism is between approximately 3.2 centimeters (cm) to 9.6 cm.

* * * * *